United States Patent [19]
Lawrenson

[11] 3,974,233

[45] Aug. 10, 1976

[54] PROCESS FOR THE PRODUCTION OF A RHENIUM HEPTOXIDE/ALUMINA DISPROPORTIONATION CATALYST

[75] Inventor: Malcolm John Lawrenson, Leatherhead, England

[73] Assignee: BP Chemicals International Limited, London, England

[22] Filed: Oct. 17, 1974

[21] Appl. No.: 515,646

Related U.S. Application Data

[63] Continuation-in-part of Ser. No. 381,343, July 20, 1973, abandoned.

[52] U.S. Cl. .......................... 260/683 D; 252/437; 252/461; 260/666 A; 260/677 R; 260/680 R
[51] Int. Cl.² ............................................ C07C 3/62
[58] Field of Search ........ 260/683 D, 666 A, 677 R, 260/680 R; 252/437, 461

[56] References Cited
UNITED STATES PATENTS

| | | | |
|---|---|---|---|
| 2,441,297 | 5/1948 | Stirton | 252/437 |
| 2,938,874 | 5/1960 | Rosinski | 252/437 |
| 3,326,961 | 6/1967 | Eden et al. | 252/437 |
| 3,342,750 | 9/1967 | Kearby | 252/437 |
| 3,423,331 | 1/1969 | Eden | 252/437 |
| 3,485,889 | 12/1969 | Williams et al. | 260/683 |
| 3,707,581 | 12/1972 | Heckelsberg | 260/683 |

FOREIGN PATENTS OR APPLICATIONS

| | | | |
|---|---|---|---|
| 1,208,038 | 10/1970 | United Kingdom | 260/683 |

*Primary Examiner*—Delbert E. Gantz
*Assistant Examiner*—C. E. Spresser
*Attorney, Agent, or Firm*—Morgan, Finnegan, Pine, Foley & Fee

[57] ABSTRACT

A rhenium heptoxide supported on alumina catalyst is prepared by digesting the alumina support with an aqueous solution of ammonium phosphate, ammonium dihydrogen phosphate or diammonium hydrogen phosphate at a temperature in the range ambient to the boiling point of the solution, separating the treated alumina by for example sieving and loading the treated alumina with between 1 and 15% by weight of rhenium heptoxide. The catalyst prepared in this manner is active for the disproportionation of olefinic hydrocarbons.

8 Claims, 1 Drawing Figure

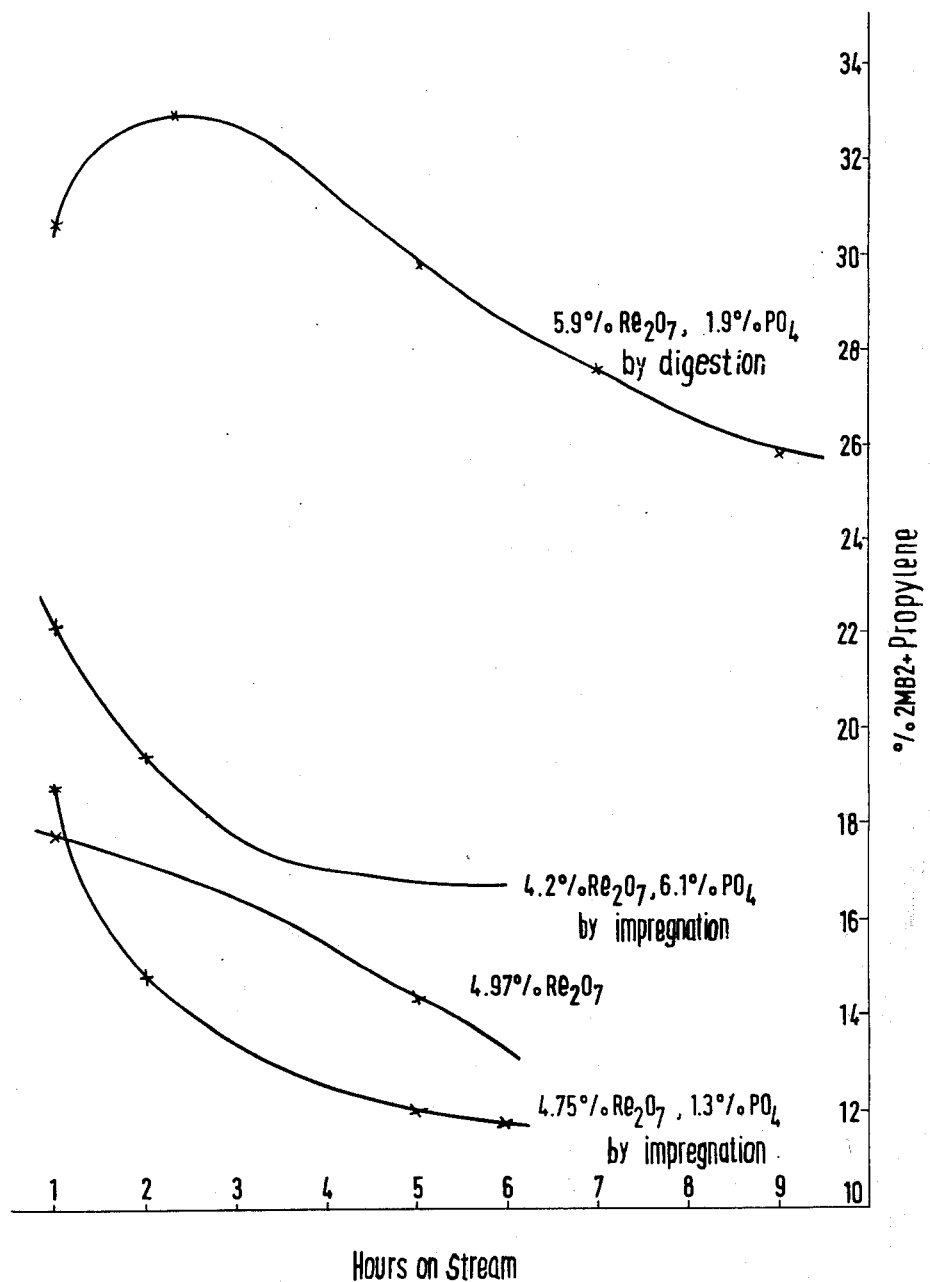

PROCESS FOR THE PRODUCTION OF A RHENIUM HEPTOXIDE/ALUMINA DISPROPORTIONATION CATALYST

This application is a continuation-in-part of my co-pending U.S. application Ser. No. 381,343 filed on July 20, 1973, now abandoned.

The present invention relates to a process for the production of a disproportionation catalyst and to a process for the disproportionation of olefinic hydrocarbons in the presence of a catalyst so produced.

By disproportionation of olefinically unsaturated hydrocarbon compounds within the context of this invention is to be understood a reaction between two molecules.

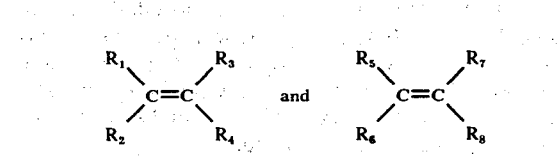

which can be thought to take place by rupture of the double bonds between the radicals

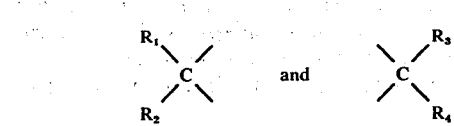

and between the radicals

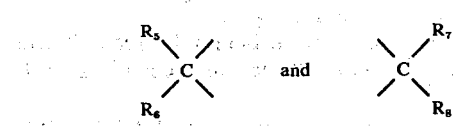

with simultaneous formation of double bonds between the radicals

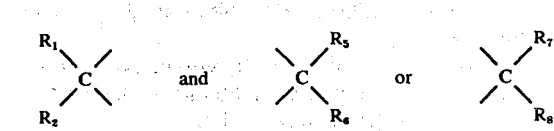

and between the radicals

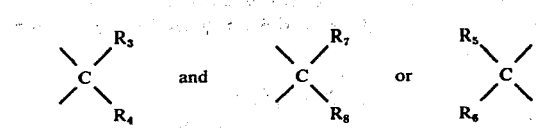

leading to structures

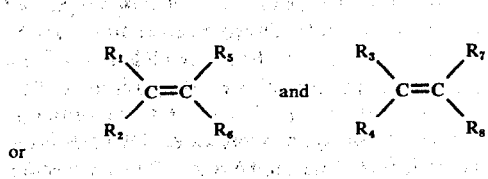

or

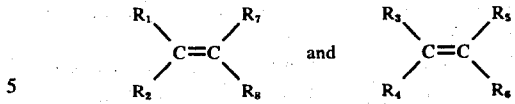

$R_1$, $R_2$, $R_3$, $R_4$, $R_5$, $R_6$, $R_7$, $R_8$, which may be mutually the same or different, may denote hydrogen, alkyl, mono- or polyolefinically unsaturated alkyl, cycloalkyl, mono- or polyolefinically unsaturated cycloalkyl, aryl, alkaryl, mono- or polyolefinically unsaturated alkaryl, alkyl-substituted aryl, aryl substituted with mono- or polyolefinically unsaturated alkyl; one or both of the original olefin molecules may be a cyclic olefin. By way of example the following types of reaction are mentioned, all of which constitute a disproportionation of olefinically unsaturated hydrocarbon compounds (further also to be called olefins) in the purview of this invention:

a. reaction of a molecule of a non-cyclic mono-olefinically unsaturated compound with an identical molecule, giving rise to the formation of mono-olefins with a higher and lower number of carbon atoms than the number of carbon atoms present in the starting olefin, b. reaction of a molecule of an unsaturated compound containing two or more non-conjugated double bonds (e.g. a polymeric compound) with a molecule of the same or another compound containing two or more nonconjugated double bonds, c. reaction of a non-cyclic mono-olefin with a non-cyclic mono-olefin of other composition, giving rise to the production of two mono-olefins, the sum of the number of carbon atoms of these olefins being equal to the sum of the number of carbon atoms in the original olefins, d. reaction of a non-cyclic mono-olefinically unsaturated compound with a polyolefinically unsaturated compound, e. reaction of a non-cyclic mono-olefin with a cyclic olefin. In this reaction one compound is formed containing a number of carbon atoms which is equal to the sum of the number of carbon atoms present in the cyclic and the non-cyclic olefin, f. reaction of a cyclic olefin with another cyclic olefin of the same or different structure, g. reaction of a cyclic olefin with a poly-unsaturated olefinic compound. In this reaction one compound is formed containing the sum of carbon atoms and double bonds which were present in the reactants.

Our U.S. Pat. No. 3,641,189 discloses a process for the disproportionation of acyclic olefins by contacting the olefin with a rhenium heptoxide supported on alumina catalyst.

Our British Patent No. 1,216,587 discloses a process for the disproportionation of olefins by contacting an olefin with an alumina-containing disproportionation catalyst under conditions which effect disproportionation of the feed, the alumina having been treated prior to combining with the catalyst by impregnation of phosphate ions. Impregnation is a commonly used technique for incorporating an active component on a support. Basically this procedure involves bringing the support into contact with a solution of a compound or salt and removing the excess solvent, usually by evaporation, thereby effecting a drying of the catalyst. Thus the desired catalytic material is forced to extend throughout the pores and/or over the surface of the carrier and is totally transferred from the solution to the carrier.

It has now been found that an improved rhenium heptoxide supported on alumina disproportionation catalyst results from treating the alumina support by digestion with an ammonium phosphate.

Thus according to the present invention there is provided a process for the production of a rhenium heptoxide supported on alumina disproportionation catalyst which process comprises treating the alumina support prior to loading with rhenium heptoxide by digesting the alumina with an aqueous solution of an ammonium phosphate and separating the teated alumina therefrom.

Digestion involves steeping the support in a solution of the salt and thereafter removing both excess solvent and solute e.g. by washing. At no point is the support allowed to become dry or uncovered so that it is always in equilibrium with the excess of external solution. It is believed that digestion allows only preferential incorporation of the solute on to specific sites within the carrier and is therefore more selective than impregnation.

The term an ammonium phosphate throughout this specification is intended to include ammonium phosphate itself, ammonium dihydrogen phosphate and diammonium hydrogen phosphate of which diammonium hydrogen phosphate is preferred.

The preferred alumina is gamma-alumina derived from boehmite prepared by the hydrolysis of aluminium alkoxides resulting from oxidation of the products of a Ziegler-type reaction of a lower molecular weight aluminium alkyl and an alpha mono-olefin.

Rhenium heptoxide may be loaded on to the modified support by any known method. Suitable methods include those described in our U.S. Pat. Nos. 3,424,312 and 3,448,163, though it is preferred to impregnate the modified support with an aqueous solution of rhenium heptoxide or a compound of rhenium capable of forming rhenium heptoxide followed by drying. Suitable rhenium compounds capable of being decomposed by heat to rhenium heptoxide include ammonium perrhenate and perrhenic acid.

Sufficient of an ammonium phosphate may be employed in the digestion to result in an alumina containing up to 16%, preferably up to 12% and even more preferably up to 8% of phosphate ion.

Digestion is suitably effected at temperatures between ambient and the boiling point of the aqueous ammonium phosphate solution, preferably at temperatures between 40C and the boiling point. Elevated pressure may be used but digestion at atmospheric pressure is preferred.

In a modificaton of the process for the production of the catalyst the alumina may be digested with an aqueous solution of aluminium nitrate prior to digestion with the aqueous ammonium phosphate solution. However, this aluminium nitrate step is unnecessary for the boehemite type of alumina prepared by the hydrolysis of aluminium alkoxides.

The period of digestion with aqueous ammonium phosphate depends on a number of factors including the temperature, the concentration of the ammonium phosphate solution and the degree of addition of phosphate ion required. Digestion is suitably continued for a period of ½ to 24 hours, preferably 1 to 12 hours and even more preferably 1 to 6 hours.

After digestion the treated alumina may be separated from the digestant by sieving. It is preferred to wash, dry and calcine the alumina prior to loading with rhenium heptoxide.

The catalyst may contain from 1 to 15 percent by weight rhenium heptoxide, preferably 1 to 12 per cent and even more preferably 1 to 10 per cent.

According to another aspect of the present invention there is provided a process for the disproportionation of an olefinic hydrocarbon feedstock which process comprises contacting an olefinic hydrocarbon or a mixture thereof at a temperature in the range −20° to +500°C and a pressure in the range 0 to 2000 psig, with a disproportionation catalyst in the manner as hereinbefore described.

Olefinic hydrocarbons suitable as feedstock include $C_2C_{30}$ acyclic olefins, preferably $C_2$ and $C_8$ straight chain alkenes. Suitable alkenes include ethylene, propylene, butene-1, butene-2, pentene-1, pentene-2, hexene-1, hexene-2, hexene-3, heptene-1, heptene-2, heptene-2 etc. Branched chain $C_3$ to $C_{30}$ alkenes are also suitable as feedstock. A preferred feedstock is one comprising butene-2 and isobutene.

Reaction conditions may vary with the composition of the feed, the desired product and the nature of the catalyst.

The catalyst is preferably activated before contact with the olefinic hydrocarbon, suitably by heating in a stream of air or oxygen at a temperature in the range 400° to 800°C for a period of ½ to 48 hours.

The reaction temperature is preferably in the range +20° to 100°C.

The process may be carried out batch wise or in a continuous manner, using the catalyst in the form of a fixed bed, a fluidised bed or a moving bed.

The process may be effected in the gaseous or liquid phase, preferably in the liquid phase.

Reaction times may vary between 0.01 seconds and 120 minutes, preferably between 0.1 seconds and 10 minutes.

Suitable olefin/catalyst weight ratios in a batch process are in the range 1000:1 to 1:1.

In a continuous process the Liquid Hourly Space Velocity (LHSV) may be in the range 1 to 100, preferably 5 to 20. The Gas Hourly Space Velocity (GHSV) may be in the range 500 to 10,000 vol/vol., preferably 2000 to 6000 vol/vol.

If desired the process may be effected in the presence of an inert diluent. Suitable inert diluents include paraffinic and cycloparaffinic hydrocarbons.

The products of the disproportionation process may be separated into fractions and selected fractions e.g. unconverted feed or fractions not having the desired carbon number may be recycled to the process.

The invention is illustrated by the following Examples.

EXAMPLE 1

50 g 30–60 BSS mesh boehmite alumina was calcined at 580°C and allowed to cool. The granules were digested for 2 h. in 200 ml. of an aqueous solution containing 30g. aluminium nitrate near its boiling point. Water was added as necessary to keep the granules covered. The mixture was then allowed to cool and settle. The supernatant liquid was decanted and replaced by 200 ml. of an aqeuous solution containing 3.1g diammonium hydrogen phosphate. The granules were digested in this solution for 4 h at 50°C. The resultant slurry was put into a 72 BSS mesh sieve ans washed with distilled water to separate the treated granules. These were then dried at 100°C overnight and then calcined at 500°C for 8 h in a current of air.

20 g of the granules were subsequently impregnated with an aqueous solution of 1.34 g ammonium perrhenate, evaporated to dryness, dried in an oven at 110°C, and activated for 16 h in a stream of air. The catalyst so prepared was found to contain 5.9 per cent $Re_2O_7$ and 1.9 per cent phosphate ion.

A commercially available butene stream (typical analysis shown in Table 1) which had been selectively hydrogenated and purified as described in our U.S. Pat. No. 3,621,073 was passed over 10 ml. of the catalyst contained in a steel reactor at ambient temperature. The products were analysed at regular intervals for propylene and 2-methylbutene-2 and the results are given in Table 2.

Table 1

| Feedstock Analysis | % wt |
|---|---|
| Ethylene | trace |
| Propane | trace |
| Propene | trace |
| Butene-1 | 6.6 |
| Isobutene | 48.6 |
| Butene-2 | 35.2 |
| Butanes | 9.6 |
| | 100.0 |

Table 2

| | Dismutation of Butenes | |
|---|---|---|
| | % 2-MB-2 % Propylene | |
| Hours on stream | 5.9% $Re_2O_7$ + 1.9% $PO_4^{3-}$ | 4.97% $Re_2O_7$ |
| 1 | 30.7 | 17.8 |
| 2.3 | 33 | — |
| 3 | 32.7 | 16.5 |
| 5 | 29.8 | 14.4 |
| 7 | 27.6 | — |
| 9 | 25.8 | — |

Comparison Test 1

50g 30–60 BSS mesh boehmite alumina was calcined at 580°C and allowed to cool.

20g of the granules were subsequently impregnated with an aqueous solution of 1.34g ammonium perrhenate, evaporated to dryness, dried in an oven at 110°C and activated in a stream of air for 16h. The catalyst so prepared was found to contain 4.9% $Re_2O_7$.

The catalyst was used for the disproportionation of the butene stream used in Example 2 under the same conditions. The results of the analysis for propylene and 2-methylbutene-2 in the products are given in Table 2.

The results of the Comparison Test and Example 1 are further illustrated in the Figure as a plot of 2-MN-2 +propylene versus hours on stream. It can be seen that the activity of the catalyst prepared by the method of the invention is approximately double the activity of the conventional rhenium heptoxide/alumina catalyst, though the amount of rhenium heptoxide in the catalyst is not very much increased.

EXAMPLE 2

10g of the catalyst used in Example 1 was reactivated at 580°C for 24 hours. A butene stream similar to that characterised in Example 1 was passed over the catalyst over a seven-day period. During this time the reactor temperature was increased from ambient at the rate of 9°C per day to finish at 88°C.

The initial butene conversion was 37% and an initial productivity of 115g isoamylenes/100g catalyst/hour was achieved. Over the period of 7 days the conversion fell to 23% and the productivity to 64g isoamylenes/100g catalyst/hour. Average conversion (7 days) was 28.6% and total productivity (7 days) was 144g $C_5$ olefins/g catalyst. A typical product analysis is give in Table 3.

Table 3

| Typical Product Analysis | % wt. |
|---|---|
| Ethylene | 0.38 |
| Propylene | 38.74 |
| 2-Methylbutene-1 | 2.26 |
| Pentene-2 (trans) | 2.63 |
| Pentene-2 (cis) | 0.75 |
| 2-Methylbutene-2 | 51.94 |
| >$C_5$ Hydrocarbons | 3.30 |

This Example shows that even after a regeneration and 7 days on stream the catalyst prepared by the process of the invention has a higher activity for olefin disproportionation than the freshly prepared conventional rhenium heptoxide/alumina catalyst.

Comparison Test 2

50g boehmite alumina, 30–60 BSS mesh, were calcined at 580°C for 24 hours and then impregnated with a solution of 0.93g diammonium hydrogen phosphate in 100 ml water. The mixture was evaporated to dryness and the resulting granules heated to 200°C for 1 hour. They were then calcined at 580°C for 20 h and sieved to give 30–60 mesh granules free from fines.

46.8g of the granules were impregnated with an aqueous solution of 3.14g ammonium perrhenate, evaporated to dryness and dried at 100°C. The catalyst was then activated in air at 580°C prior to testing and analysis. The catalyst was found to contain 4.75 percent $Re_2O_7$ and 1.3 percent $PO_4^{3-}$(= 1.0 per cent $P_2O_5$). The catalyst was used for the disproportionation of the butene stream used in Example 1 under the same conditions. The results are shown in the Figure as a plot of %2-MB-2+ propylene versus hours on stream.

EXAMPLE 3

50 g boehmite alumina, 18–60 BSS mesh, were calcined at 580°C for 18 hours. The sample was allowed to cool and then added to a solution of 5 g of diammonium hydrogen phosphate in 200 ml water. The suspension was heated to 80°C and stirred at this temperature for 6 hours. It was then drained into a 72 BSS mesh sieve and the granules washed with distilled water until the washings were clear and free from fines. The granules were oven-dried at 110°C for 18 hours and then calcined at 600°C for 18 hours.

50 g of the granules were impregnated with an aqueous solution containing 3.4 g of ammonium perrhenate, evaporated with stirring to dryness, and oven-dried at 110°C. 10 g of the catalyst were then activated in air at 580°C prior to testing and analysis.

The catalyst was found to contain 4.6 percent of $Re_2O_7$ and 6.3 percent of $PO_4^{3-}$. A selectively hydrogenated butene stream was passed over the catalyst at LHSV10 in a steel reactor under pressure at ambient temperature over a 7-day period. During this time the reactor temperature was increased from ambient at the rate of 9°C per day to finish at 88°C.

The initial butene conversion was 37%. Over the period of seven days the average conversion was 31%, and the total productivity was 127 g isoamylenes/100 g catalyst/hour.

Comparison Test 3

The method of preparation was the same as for the above example, however the quantity impregnated was 4.65g diammonium hydrogen phosphate and 48.8 g of phosphate impregnated granules were subsequently impregnated with 3.27g ammonium perrhenate to give a catalyst containing 4.23 percent $Re_2O_7$ and 6.1 percent $PO_4^{3-}$ (= 4.6 percent $P_2O_5$).

The catalyst was used for the disproportionation of the butene stream used in Example 1 under the same conditions. The results are shown in the Figure as a plot of %2-MB-2+ propylene.

Comparison Tests 2 and 3 show that the activity of the catalysts prepared by impregnation is not as high as the catalyst prepared by digestion.

EXAMPLE 4

50 g Hydronyl alumina was calcined at 600°C for 18 hours, the alumina was then digested in a solution containing 5 g diammonium hydrogen phosphate in 200 ml distilled water by heating to 80°C for 6 hours. The alumina was washed with about 300 ml water on a 72 mesh sieve to remove fines, then dried in an oven at 110°C for 18 hours and finally calcined at 600°C for 18 hours in a furnace.

The calcined phosphated alumina was impregnated with a solution of 3.4 g ammonium perrhenate in water. The catalyst was dried at 110°C then activated in dry air at 580°C for 18 hours before testing and analysis.

The catalyst was found to contain 4.6% of $Re_2O_7$ and 6.3% of $PO_4^{3-}$. A selectively hydrogenated butene stream was passed over the catalyst at LHSV10 in a steel reactor under pressure. The temperature over the seven hour period for which the reaction was on stream was increased from ambient to 88°C. Over the period of 7 hours the average butene conversion of a butene feed shown in Table 1 was 34%.

EXAMPLE 5

The catalyst was prepared as in Example 4 above except that the alumina was digested with a solution of dihydrogen ammonium phosphate before impregnation with ammonium perrhenate.

The average butene conversion using this catalyst containing 4.85% $Re_2O_7$ and 4.00% $PO_4^{3-}$ was 24% under the same reaction conditions as in Example 4.

EXAMPLE 6

The catalyst was prepared as in Example 4 above except that the alumina was digested with a solution of triammonium phosphate before impregnation with ammonium perrhenate.

With this catalyst containing 4.48% $Re_2O_7$ and 5.32 $PO_4^{3-}$, and using the same conditions as in Example 4 the average butene conversion of a butene feed as shown in Table 1 was 22%.

EXAMPLE 7

The process of preparing the catalyst described in Example 4 was followed. The catalyst contained 5.11% $Re_2O_7$ and 6.27 $PO_4^{3-}$.

Using the same conditions as in Example 4 the average butene conversion of a butene feed as shown in Table 1 was 35%.

EXAMPLE 8

Using the same catalyst and the same reaction condition (except that the reaction was on stream for 170 hours) as in Example 7 above, a propylene feed (containing 99.4% propylene and 0.6% propane) was disproportioned.

The average propylene conversion for the period of the reaction was 22%.

EXAMPLE 9

A catalyst was prepared as in Example 4 except that the alumina was digested with a solution containing 7.5 g diammonium hydrogen phosphate. The catalyst thus formed containing 5.12% $Re_2O_7$ and 8.57 $PO_4^{3-}$. Under the same conditions and using the same feed as in Example 8 above propylene was disproportionated over a period of 75 hours at LHSV 5. The average propylene conversion over this period was 27%.

EXAMPLE 10

A catalyst was prepared as in Example 9 above except that the phosphated alumina was impregnated with a solution containing 2.03 g ammonium perrhenate. The catalyst thus produced contained 3.09% $Re_2O_7$ and 9.42% $PO_4^{3-}$.

A butene feed as shown in Table 1 when disproportionated with this catalyst over a period of 170 hours on stream and at LHSV 6 gave an average conversion of 30%.

EXAMPLE 11

A catalyst was prepared as in Example 4 above except that the alumina was digested with a solution containing 7.5 g diammonium hydrogen phosphate. The catalyst so prepared contained 8.71% $Re_2O_7$ and 8.84% $PO_4^{3-}$.

Using the propylene feed as in Example 8 over this catalyst for a period of 75 hours on stream at LHSV 10 the average propylene conversion was 33%.

I claim:

1. A process for the disproportionation of an olefinic hydrocarbon feedstock which process comprises contacting an olefinic hydrocarbon or a mixture thereof selected from $C_2$ to $C_{30}$ acyclic and branched chain olefins at a temperature in the range −20° to +500°C and a pressure in the range 0 to 2000 psig with a rhenium heptoxide supported on alumina disproportionation catalyst prepared by digesting the alumina support with an aqueous solution of an ammonium salt selected from ammonium phosphate, ammonium dihydrogen phosphate and diammonium hydrogen phosphate at a temperature between ambient and the boiling point of the aqueous ammonium salt solution, the amount of phosphate ions in the alumina support being at a maximum of 16% by weight separating the treated alumina thereform and loading the treated alumina with between 1 and 15% by weight of rhenium heptoxide.

2. A process according to claim 1 wherein the olefinic hydrocarbon or mixture thereof is selected from $C_2$ to $C_8$ straight chain alkenes.

3. A process according to claim 1 wherein the mixture of olefinic hydrocarbons consists of isobutene and butene-2.

4. A process according to claim 1 wherein the disproportionation temperature is in the range +20° to 100°C.

5. A process according to claim 1 when effected in the liquid phase at a liquid hourly space velocity of the feedstock in the range 5 to 20.

6. A process according to claim 1 when effected in the gas phase at a Gas Hourly Space Velocity in the range 2000 to 6000 vol/vol.

7. A process according to claim 1 wherein the olefin/catalyst weight ratio in a batch process in the range 1000:1 to 1:1.

8. A process according to claim 1 wherein the reaction time is in the range 0.1 seconds to 10 minutes.

* * * * *

UNITED STATES PATENT OFFICE
CERTIFICATE OF CORRECTION

Patent No. 3,974,233　　　　　　　　　　Dated August 10,,1976

Inventor(s) Malcolm John Lawrenson

It is certified that error appears in the above-identified patent and that said Letters Patent are hereby corrected as shown below:

On the cover sheet insert:

-- [30] Foreign Application Priority Data

United Kingdom　　　38411　　　　Aug. 17, 1972 --.

*Signed and Sealed this*

*twenty-third* Day of *August 1977*

[SEAL]

*Attest:*

RUTH C. MASON　　　　　　　　　　C. MARSHALL DANN
*Attesting Officer*　　　　　　　　*Commissioner of Patents and Trademarks*